US00PP31840P2

(12) United States Plant Patent
Fielding

(10) Patent No.: US PP31,840 P2
(45) Date of Patent: Jun. 2, 2020

(54) ***DIGITALIS* 'FIREBIRD'**

(50) Latin Name: ***Digitalis* x *valinii***
Varietal Denomination: Firebird

(71) Applicant: John Fielding, London (GB)

(72) Inventor: John Fielding, London (GB)

( * ) Notice: Subject to any disclaimer, the term of this patent is extended or adjusted under 35 U.S.C. 154(b) by 0 days.

(21) Appl. No.: 16/501,878

(22) Filed: Jun. 19, 2019

(51) Int. Cl.
*A01H 5/02* (2018.01)
*A01H 6/68* (2018.01)

(52) U.S. Cl.
USPC ..... Plt./263.1

(58) Field of Classification Search
USPC ..... Plt./263.1
CPC ..... A01H 5/02; A01H 6/68
See application file for complete search history.

*Primary Examiner* — Annette H Para
(74) *Attorney, Agent, or Firm* — Cassandra Bright

(57) ABSTRACT

A new and distinct *Digitalis* cultivar named 'Firebird' is disclosed, characterized by plants exhibiting improved Winter hardiness and basal branching without pinching. Plants are taller than known varieties and have a unique flower color combining greyed oranges and reds. The new variety is a *Digitalis hybrida*, normally produced as an outdoor garden or container plant.

2 Drawing Sheets

Figure 1:
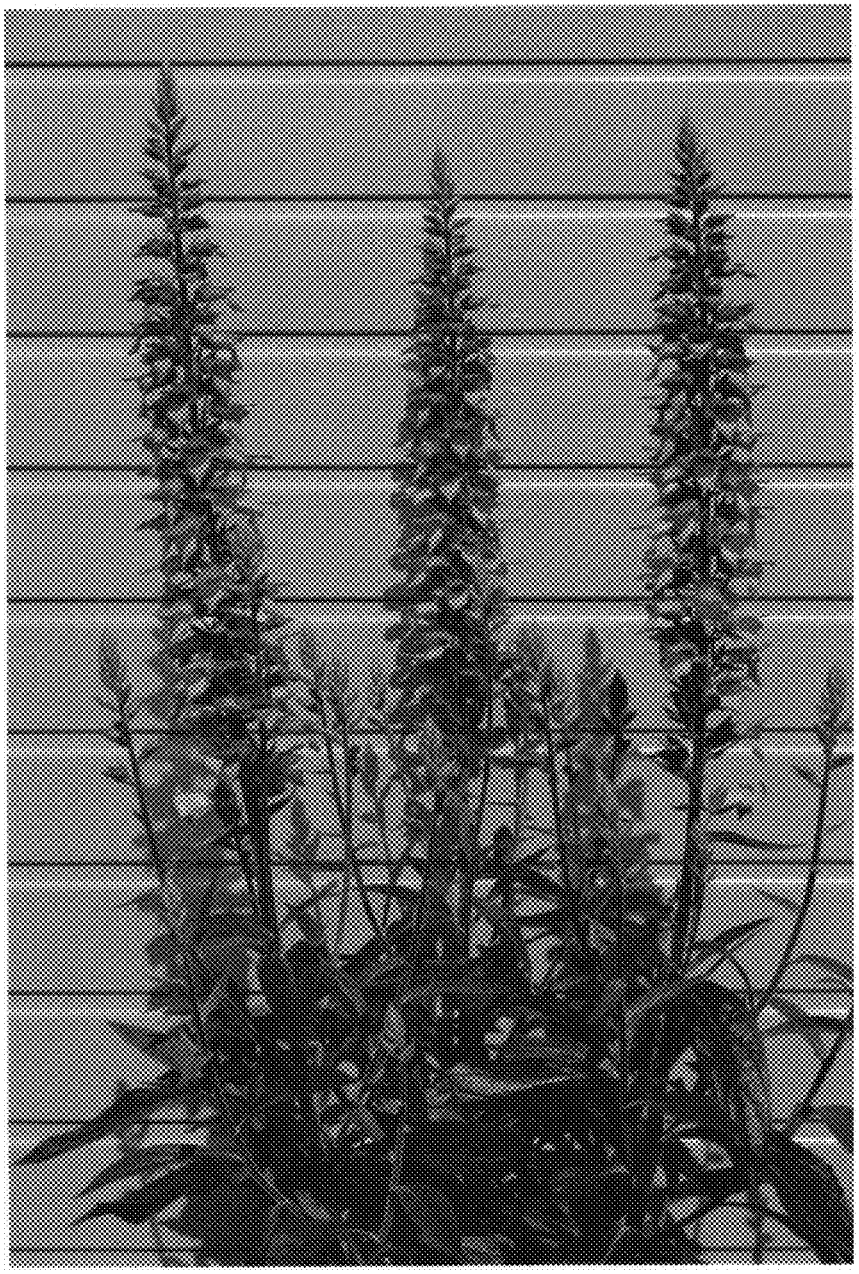

Latin name of the genus and species: *Digitalis* x *valinii*.
Variety denomination: 'Firebird'.

BACKGROUND OF THE INVENTION

The new *Digitalis* cultivar is a product of a planned breeding program by the inventor, John Fielding. The crossing resulting in this new variety was performed in 2010.

The seed parent variety is an unnamed, unpatented proprietary variety of *Digitalis purpurea*. The pollen parent is an unnamed, unpatented proprietary variety of *Digitalis canariensis*. The new variety was identified as a potentially interesting selection during June of 2015 at a private garden in London, United Kingdom. First public exposure was May 21, 2019, in the United Kingdom. Information and access to the new variety was initiated directly by the inventors or one who obtained the claimed invention directly or indirectly from the inventors. All public disclosures made between May 21, 2019 and the filing of this application fall within the exception allowed under 102(b)(1).

Asexual reproduction of the new cultivar *Digitalis* 'Firebird' was first performed during Summer of 2015, in London, United Kingdom, at the inventor's private garden using terminal vegetative cuttings. Subsequent propagation has shown that the unique features of this cultivar are stable and reproduced true to type on successive generations.

SUMMARY OF THE INVENTION

The cultivar *Digitalis* 'Firebird' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Firebird'. These characteristics in combination distinguish 'Firebird' as a new and distinct *Digitalis* cultivar:

1. Improved winter hardiness.
2. Produces branches from the base of the flower stem without pinching.
3. Taller than known varieties.
4. Interesting flower color combining greyed reds and oranges.

PARENT COMPARISONS

Plants of the new cultivar 'Firebird' are similar to plants of the seed parent in most horticultural characteristics, however, plants of the new cultivar 'Firebird' differ in the following:

1. The new variety has a more branched habit than the seed parent.
2. The new variety is more reliably perennial, while the seed parent often dies after flowering.
3. The new variety flowers continuously, while the seed parent only flowers once per season.
4. The new variety forms no viable seeds, while the seed parent produces plentiful viable seed.

Plants of the new cultivar 'Firebird' are similar to plants of the pollen parent in most horticultural characteristics, however, plants of the new cultivar 'Firebird' differ in the following:

1. The new variety is more cold-hardy than the pollen parent.
2. The new variety has red flowers with orange throats, while the pollen parent has apricot-orange flowers.
3. The new variety forms no viable seeds, while the pollen parent produces viable seed.
4. The new variety flowers continuously, while the pollen parent flowers once or twice per year.

COMMERCIAL COMPARISONS

Plants of the new cultivar 'Firebird' can be compared to the commercial variety *Digitalis valinii* 'TAKFORUGL', U.S. Plant Pat. No. 25,640. These varieties are similar in most horticultural characteristics; however 'Firebird' differs in the following:

1. Flowers of the new variety are red with orange throats, while this comparator's flowers are more red-purple.
2. The new variety is a taller plant than this comparator.

Plants of the new cultivar 'Firebird' can also be compared to the commercial variety *Digitalis valinii* 'TMDGFP001', unpatented. These varieties are similar in most horticultural characteristics; however 'Firebird' differs in the following:

1. Flowers of the new variety are red with orange throats, while this comparator's flowers are more pink.
2. The new variety is a taller plant than this comparator.

Plants of the new cultivar 'Firebird' can also be compared to the commercial variety *Digitalis* 'TMDG1301', unpatented. These varieties are similar in most horticultural characteristics; however 'Firebird' differs in the following:

1. Flowers of the new variety are red with orange throats, while this comparator's flowers are a paler pink.
2. The new variety is a taller plant than this comparator.

BRIEF DESCRIPTION OF THE PHOTOGRAPHS

The accompanying photograph in FIG. 1 illustrates in full color typical plants of 'Firebird' grown outdoors in London, United Kingdom. Age of the plants photographed are approximately 26 weeks.

Figure 2:
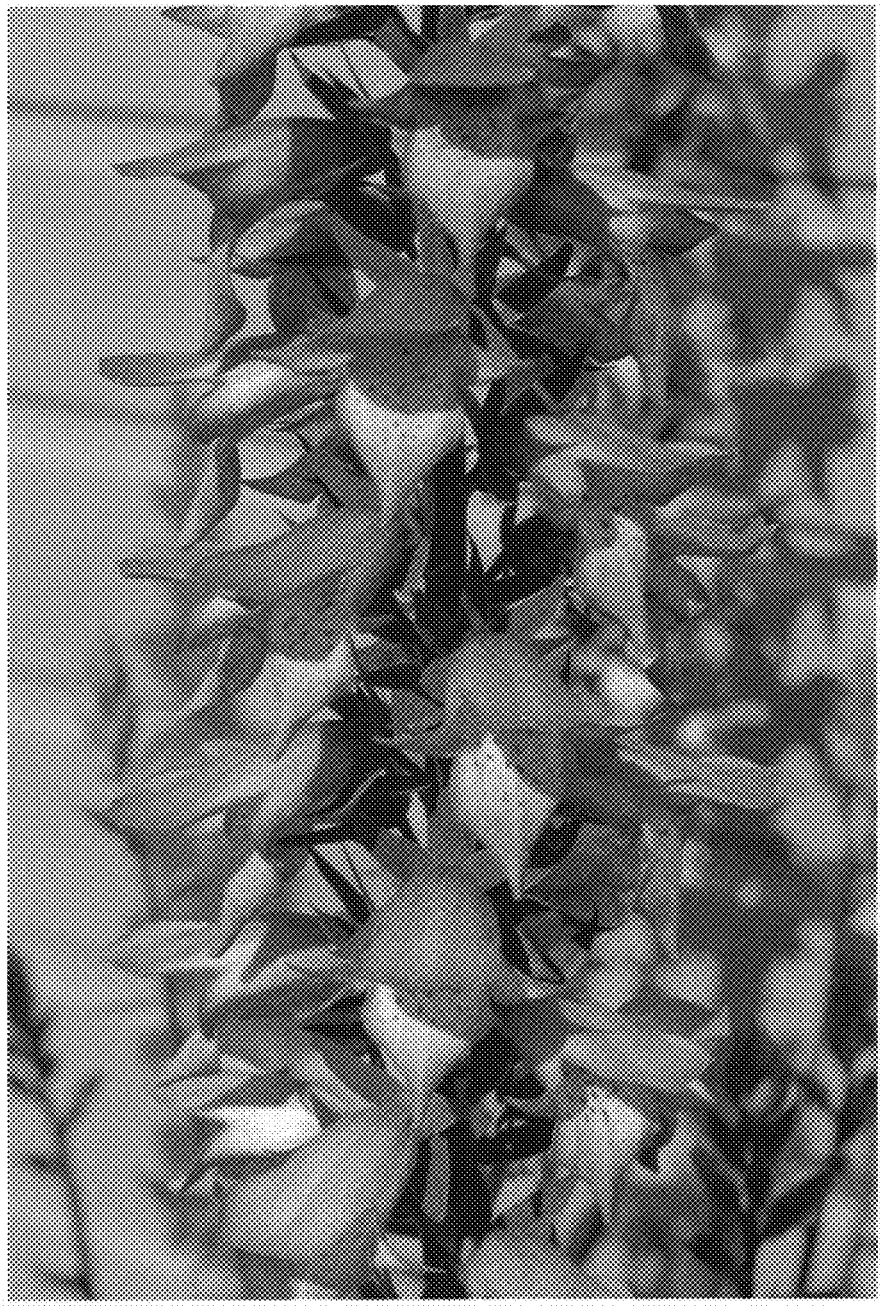

FIG. 2 illustrates in full color typical flowers of 'Firebird'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Firebird' plants grown in High Hurstwood, East Sussex, United Kingdom. Measurements and numerical values represent averages of typical plant types.

Botanical classification: *Digitalis* x *valinii* 'Firebird'.

PROPAGATION

Propagation method: Terminal cuttings or tissue culture.

PLANT

Growth habit: Herbaceous perennial with woody stems.
Age of plant described: Approximately 6 months.
Pot size of plant described: 36 cm container.
Height: 120 cm.
Plant spread: 50 cm.
Vigor: Vigorous.
Stem:
- *Basal branching.*—Yes.
- *Average number of lateral branches.*—8.
- *Pinching.*—Yes. Although plants will branch without pinching, trials have shown that a single pinch will improve plant habit with abundant branching.
- *Lateral branch dimensions.*—Diameter: 6 mm. Length: 32 cm from base to the lowest flower. Stem shape: Round.
- *Stem strength.*—Strong and rigid.
- *Stem color.*—Between RHS Green 138B and 138C.
- *Pubescence.*—Short, finely pubescent.

FOLIAGE

Leaf:
- *Compound or single.*—Single.
- *Arrangement.*—Alternate.
- *Attachment.*—Decurrent.
- *Number of leaves per branch.*—15 to 20.
- *Margin.*—Serrate.
- *Surface* (*abaxial and adaxial*).—Glabrous.
- *Shape.*—Oblanceolate to elliptic.
- *Length.*—27 cm.
- *Width.*—9 cm.
- *Color.*—Young leaf upper surface: RHS Yellow-Green 146A and 147B, colors mixed together. Young leaf lower surface: RHS Green 138B. Mature leaf upper surface: RHS Green N137A and Yellow-Green 147A, colors mixed together. Mature leaf lower surface: RHS Greyed-Green 191A.
- *Apex.*—Apiculate.
- *Base.*—Cuneate.
- *Pubescence* (*upper and lower surfaces*).—Puberulous.
- *Venation pattern.*—Lacinate.
- *Vein color* (*upper surface*).—RHS Yellow-Green N144D.
- *Vein color* (*lower surface*).—RHS Yellow-Green 145C.

FLOWER

Natural flower season: May until frost.
Time to flower from cutting: 10 to 14 weeks, depending on time of year and growing conditions.
Inflorescence type and habit: Raceme.
Quantity of flowers: About 60 to 75 per lateral stem.
Inflorescence size:
- *Diameter.*—8 cm.
- *Height.*—65 cm.

Flower aspect: Outward.
Flower shape: Bilabiate campanulate, formed of four fused petals.
Flower dimensions, fully open:
- *Length.*—32 to 35 mm.
- *Width.*—28 to 32 mm.
- *Height.*—27 to 29 mm.

Fragrance: Very mild sweet scent.
Bud:
- *Length.*—21 mm.
- *Diameter.*—9 mm.
- *Color.*—When first separated from terminal cluster: RHS Yellow-Green 145B at base, fading to Greyed-Purple 182B at tip. Immediately prior to opening: RHS Yellow-Green 145B at base, fading to Greyed-Purple 184A at tip.

Petals:
- *Length.*—Upper lip: 33 mm. Lower lip: 36 mm.
- *Width, upper and lower.*—14 mm.
- *Shape.*—Fused becoming campanulate.
- *Texture.*—Outer and inner surfaces smooth. Inner surface with fine hairs on lip.
- *Margin.*—Entire.
- *Apex.*—Top and bottom lips: Obtuse. Left and right extremities: Acuminate.
- *Base.*—Fused.

*Self-cleaning or persistent*.—Petals self-clean; style persists.

*Color*.—When opening, inner surface: All inner surfaces: RHS Yellow-Green 145C to 145D, colors present individually. Upper petal tip: RHS Greyed-Purple 185A. Lower petal spots: RHS Greyed-Purple 187B. Lower petal tip: Between RHS Greyed-Red 178B and 179A. When opening, outer surface: Upper petal: Base RHS Greyed-Orange N167A flushed with Greyed-Red 182A; tip 182A. Lower petal: Base RHS Yellow-Green 145C; tip Greyed-Purple 184A to 184B. Fully open, inner surface: Upper petal: RHS Orange-White 159C, with Orange-Red N34A at tip and midrib. Lower petal: RHS Orange-White 159C at base, fading to Greyed-Yellow 162C at margin and Greyed-Orange 175B at tip. Spots on lower petal: RHS Greyed-Orange 175A. Fully open, outer surface: Upper petal: Base RHS Greyed-Yellow 163C flushed with Greyed-Purple 184B and fading to 184B at the tip. Lower petal: RHS Greyed-Purple 185D fading to 185C at the tip.

Sepals:

*Shape*.—Quantity per flower: 3, fused to form a tube. Unfused apex.

*Margin*.—Entire.

*Apex*.—Acute.

*Texture*.—Softly pubescent and ridged.

Peduncle:

*Length*.—Average 26 cm.

*Diameter*.—0.2 cm.

*Color*.—Near RHS Green NN137C at base, turning 187B near attachment.

*Shape*.—Quadrangular and fluted.

*Orientation*.—Straight. Occurring at approximately 15 degree angle from center of plant.

*Strength*.—Moderately strong.

*Texture*.—Sparsely pubescent.

Pedicels:

*Length*.—Average 0.5 cm.

*Diameter*.—0.1 cm.

*Color*.—Near RHS Greyed-Purple 187B.

*Orientation*.—Straight, approximately 25 degree angle from attachment.

*Strength*.—Strong.

*Texture*.—Pubescent.

REPRODUCTIVE ORGANS

Stamens:

*Number*.—2.

*Length*.—16 mm.

*Color*.—RHS White N155A, fading to Red-Purple 70C at base.

*Staminode color*.—RHS Greyed-Purple 183A.

*Staminode length*.—3 mm.

*Pollen*.—Absent.

Pistil:

*Number*.—1.

*Length*.—4.4 cm.

*Style*.—Length: 2 mm. Width: 4 mm. Color: RHS Red-Purple 71D.

Ovary:

*Position*.—Superior.

*Shape*.—Broadly globose.

*Height*.—2.5 mm.

*Diameter*.—3 mm.

*Color*.—RHS Yellow-Green 150B.

*Surface*.—Glabrous.

*Appearance*.—Semi-glossy.

OTHER CHARACTERISTICS

Seeds and fruits: Not observed.

Disease/pest resistance: Neither resistance nor susceptibility to pathogens and pests common to *Digitalis* have been observed.

Temperature tolerance: Hardy to −7° C.

What is claimed is:

1. A new and distinct cultivar of *Digitalis* plant named 'FIREBIRD' as herein illustrated and described.

* * * * *